(12) United States Patent
Kawanishi et al.

(10) Patent No.: US 6,745,130 B2
(45) Date of Patent: Jun. 1, 2004

(54) GENETIC MOTIF EXTRACTING AND PROCESSING APPARATUS, GENETIC MOTIF EXTRACTING AND PROCESSING METHOD, AND RECORDING MEDIUM RECORDED WITH GENETIC MOTIF EXTRACTING AND PROCESSING PROGRAM

(75) Inventors: Yuichi Kawanishi, Kawasaki (JP); Kimitoshi Naito, Kawasaki (JP); Shin Miyazawa, Kawasaki (JP); Tatsuya Ito, Kawasaki (JP); Takamasa Futatsuki, Yokohama (JP)

(73) Assignee: Fujitsu Limted, Kawasaki (JP)

( * ) Notice: Subject to any disclaimer, the term of this patent is extended or adjusted under 35 U.S.C. 154(b) by 200 days.

(21) Appl. No.: 09/779,495

(22) Filed: Feb. 9, 2001

(65) Prior Publication Data
US 2001/0004448 A1 Jun. 21, 2001

Related U.S. Application Data

(63) Continuation of application No. PCT/JP99/01693, filed on Mar. 31, 1999.

(30) Foreign Application Priority Data

Aug. 19, 1998 (JP) ............................ 10-232901

(51) Int. Cl.[7] .................. G06F 17/30; G06F 19/00; G06N 3/02; G06N 3/12
(52) U.S. Cl. ................. 702/20; 707/6; 706/13
(58) Field of Search .............. 702/20; 707/6; 706/13; 435/6

(56) References Cited

U.S. PATENT DOCUMENTS 5,598,350 A    1/1997   Kawanishi et al. ......... 364/496
5,701,256 A *  12/1997  Marr et al. ................ 364/496

FOREIGN PATENT DOCUMENTS

EP   0198403      10/1986   ........... G06F/15/20
JP   07-274965    10/1995   ........... C12N/15/00
JP   10-187666    7/1998    ........... G06F/17/18

OTHER PUBLICATIONS

Attwood et al. The Prints database of protein fingerprints: A novel informationrsource ofr computational molceular biology. Journal of Chemical Informationand Computer Science (1997), vol. 37, pp. 417–424.*

Ming K. Lee, et al., "SeqHelp: A Program to Analyze Molecular Sequences Utilizing Common Computational Resources", Genome Research, 'Online!, vol. 8, No. 3, Mar. 1998, pp. 1–8.

Michael C. Giddings, et al., "A Software System for Data Analysis in Automated DNA Sequencing", Genome Research, 'Online!, vol. 8, No. 6, Jun. 1998, pp. 1–23.

Jian Jiang, et al., "EbEST: An Automated Tool Using Expressed Sequence Tags to Delineate Gene Structure", Genome Research, vol. 8, No. 3, Mar. 1998, pp. 1–10.

* cited by examiner

*Primary Examiner*—Marjorie Moran
(74) *Attorney, Agent, or Firm*—Staas & Halsey LLP

(57) ABSTRACT

A genetic motif is extracted from at least one piece of input gene arrangement information, and based on the extracted motif, gene arrangement information including the motif as a part thereof is retrieved from previously gene information. The gene arrangement information as retrieved is added to the input gene arrangement information, to thereby improve a genetic motif extracting efficiency.

8 Claims, 12 Drawing Sheets

FIG.4

INPUT GENE ARRANGEMENT DATA

```
                10        20        30        40        50        60
                 +    ·    +    ·    +    ·    +    ·    +    ·    +
XLEN2MAB-1   ·········--MEENEQNNREVEPQQE---SG--------EESNRG--------ILHQAPPG
BFU82487-1   ----------------------------------MANSSADENGNPPASPPPHSPVQPEDSPS
BRENG1-1     -----------------------------MEDQR-RGQGEEEDDSGSLPSPPLL---------
BRENG2-1     -----------MDENEQSARDVE--QR--GA--D-------ESNS--A--IRPLLQ---APG
BRENG2G-1    -----------MDENEQSARDVE--QR--GA--D-------ESNS--A--IRPLLQ---APG
BRENG3-1     -----------MEENDHSNRDVE--RQ--DS--D-------ESNR--A--ILPLLQ---APG
MUSEN2AB-1   MEEKDSKPSE-AAEAQRQPEPSSGGGSGGGSPSDSDTGRRRALMLPEVLQAPGNHQHPHR 70        80        90       100       110       120
                 +    ·    +    ·    +    ·    +    ·    +    ·    +
XLEN2MAB-1   NHQPHHRITNFFIDNILRPEFGRRK---------------------E----RINHQDEL
BFU82487-1   PDGP--RTTNFSIANILRPEFGARK-----------------------------------
BRENG1-1     --PAHRNTDFFIDNILRPDFG----------------------------------------
BRENG2-1     NLQLPHRITNFFIDNILRPDFGRKKEANI----------------------------TRYEDN
BRENG2G-1    NLQLPHRITNFFIDNILRPDFGRKKEANI----------------------------TRYEDN
BRENG3-1     NV-LPHRITNFYIDNILRPDFGRRKEGS-----------------------------RRDEIN
MUSEN2AB-1   ITNFFIDNILRPEFGRRKDAGTCCAGAGAGARGGEGGAGTTEGGGGGAGGAEQLDCNPTGS 130       140       150       160       170       180
                 +    ·    +    ·    +    ·    +    ·    +    ·    +
XLEN2MAB-1   FTGRDT-------GALSGAESGHHRV----NVPEGAGGSSKVITVTGEKKS
BFU82487-1   RDSKSCDSS--PVSSPG--KPAPG------DLSPSLPASPGG---------
BRENG1-1     -----CKR-E------------RERVTRD--SGVRPTALPDSRDGVSSSAS
```

| FILE INPUT | AUTOMATIC ALIGNMENT | MOTIF EXTRACTION | DATA EDITION | SETTING |

NO CONVERSION

FIG.5

EDIT GENE ARRANGEMENT DATA

```
              10        20        30        40        50        60
              +         +         +         +         +         +
XLEN2MAB-1    ........  ........  ........  ........  ........  ........
BFU82487-1    --------  --MEENEQNNREVEPQQE--SG------EESNRG-----  --ILHQAPPG
BRENG1-1      --------  --------  --------  MANSSADENGNPPASPPPHSPVQPEDSPS
BRENG2-1      --------  --------  --------  MEDQR-RGQGEEEDDSGSLPSPPLL
BRENG2G-1     --MDENEQSARDVE--QR-GA--D--  ----ESNS--A---IRPLLQ---APG
BRENG3-1      --MDENEQSARDVE--QR-GA--D--  ----ESNS--A---IRPLLQ---APG
MUSEN2AB-1    --MEENDHSNRDVE--RQ-DS--D--  ----ESNR--A---ILPLLQ---APG
              MEEKDSKPSE-AAEAQRQPEPSSGGGSGGG--SP---SDSDTGRRALMLPEVLQ--APG 70        80        90       100       110       120
              +         +         +         +         +         +
XLEN2MAB-1    NHQPHHRITNFFIDNILRPEFGRRK-----------------------------
BFU82487-1    PDGP--RITNFSIANILRPEFGARK-----------E-------R-INHQDEL
BRENG1-1      --PAHRNTDFFIDNILRPEFGRRK-----------E-------R-INHQDEL
BRENG2-1      NLQLPHRITNFFIDNILRPDFGRKKEANI---------------TRYEDN
BRENG2G-1     NLQLPHRITNFFIDNILRPDFGRKKEANI---------------TRYEDN
BRENG3-1      NV-LPHRITNFYDNILRPDFGRRKEGS-----------------RRDEIN
MUSEN2AB-1    NHQHPHRITNFFIDNILRPEFGRRKDAGTCCAGAGAGGARGGEGGAGTTEGGGGGAGGAEQL 130       140       150       160       170       180
              +         +         +         +         +         +
XLEN2MAB-1    FTGRDT------GALSGAESGHHRV----NVPEGAGGSSKVITVIGEKKS
BFU82487-1    RDSKSCDSS---PVSSPG--KPAPG----DLSPSLPASPGG
BRENG1-1      --CKR-E-----RERVTRD--SGVRPTALPDSRSDGVSSSAS
```

50

52

54 ADD DATA
56 AUTOMATIC ALIGNMENT
58 MOTIF EXTRACTION
60 SETTING

NO CONVERSION

FIG.6

EDIT GENE ARRANGEMENT DATA

```
                    10        20        30        40        50        60
            ....+....+....+....+....+....+....+....+....+....+....+....+
XLEN2MAB-1  ----------MEENEQNNREVEPQQE--SG-------EESNRG-----ILHQAPPG
BFU82487-1  ------------------------------MANSSADENGNPPASPPPPHSPVQPEDSPS
BRENG1-1    ------------------------------MEDQR-RGQGEEEDDSGSLPSPPLL
BRENG2-1    --------MDENEQSARDVE--QR--GA--D-------ESNS--A--TRPLLQ--APG
BRENG2G-1   --------MDENEQSARDVE--QR--GA--D-------ESNR--A--TRPLLQ--APG
BRENG3-1    --------MEENDHSNRDVE--RQ--DS--D-------ESNR--A--ILPLLQ--APG
MUSEN2AB-1  MEEKDSKPSE-AAEAQRQPEPSSGGGSGGG--SP----SDSDTGRRRALMLPEVLQ--APG 10        20        30        40        50        60
            ....+....+....+....+....+....+....+....+....+....+....+....+
XLEN2MAB-1  NHQPHRITNFF IDNILRPEFGRRK------------------------E---RINHQDEL
BFU82487-1  PDGP--RTNFSIANILRPEFGARK------------------------------------
BRENG1-1    PAHRNTDFFIDNILRPDFG-----------------------------------------
BRENG2-1    NLQLPHRITNFFIDNILRPDFGRKKEANI-------------------------TRYEDN
BRENG2G-1   NLQLPHRITNFFIDNILRPDFGRKKEANI-------------------------TRYEDN
BRENG3-1    NV-LPHRITNFYIDNILRPDFGRKKEGS--------------------------RRDEIN
MUSEN2AB-1  NHQPHRITNFFIDNILRPEFGRRKDAGTCCAGAGGARGGEGGAGTTEGGGGGAGGAEQL 10        20        30        40        50        60
            ....+....+....+....+....+....+....+....+....+....+....+....+
XLEN2MAB-1  FTGRDT------GALSGAESGHHRV-----NVPEGAGGSSKVITVTGEKKS
BFU82487-1  RDSKSCDSS--PVSSPG--KPAPG-----DLSPSLPASPGG---------
BRENG1-1    ----CKR-E-------------------------RERVTRD--SGVRPTALPDSRSDGVSSSAS
```

[ ADD DATA ] [ AUTOMATIC ALIGNMENT ] [ MOTIF EXTRACTION ]~58 [ SETTING ]

NO CONVERSION

EDIT GENE ARRANGEMENT DATA

```
                     10        20        30        40        50        60
            ....+....|....+....|....+....|....+....|....+....|....+....|
XLEN2MAB-1  ----------MEENEQNNREVEPQQE--SG----EESNRG-----ILHQAPPG
BFU82487-1  ----------------------------MANSSADENGNPPASPPPHSPVQPEDSPS
BRENG1-1    ---------MDENEQSARDVE--QR--GA--D----MEDQR-RGQGEEEDDSGSLPSPPLL
BRENG2-1    ---------MDENEQSARDVE--QR--GA--D----ESNS--A--IRPLLQ--APG
BRENG2G-1   ---------MDENEQSNRDVE--RQ--DS--D----ESNR--A--IRPLLQ--APG
BRENG3-1    ---------MEENDHSNRDVE--RQ--DS--D----ESNR--A--ILPLLQ--APG
MUSEN2AB-1  MEEKDSKPSE-AAEAQRQPEPSSGGGSGGG---SP--SDSDTGRRRALMLPEVLQ--APG 10        20        30        40        50        60
            ....+....|....+....|....+....|....+....|....+....|....+....|
XLEN2MAB-1  NHQPHHRITNFFIDNILRPEFGRRK--------------------
BFU82487-1  PDGP--RTTNFSIANILRPEFGARK----------E----RINHQDEL
BRENG1-1    PAHRNTDFFIDNILRPDFG--------------------------
BRENG2-1    NLQLPHRITNFFIDNILRPDFGRKKEANI----------------TRYEDN
BRENG2G-1   NLQLPHRITNFFIDNILRPDFGRKKEANI----------------TRYEDN
BRENG3-1    NV-LPHRITNFYIDNILRPDFGRRKEGS------------------RRDEIN
MUSEN2AB-1  NHQHPHRITNFFIDNILRPEFGRRKDAGTCCAGAGGAGGAGGAGGEGGAGTTEGGGGGAGGAGGAEQL 10        20        30        40        50        60
            ....+....|....+....|....+....|....+....|....+....|....+....|
XLEN2MAB-1  FTGRDT------GALSGAESGHHRV-----NVPEGAGGSSKVITVTGEKKS
BFU82487-1  -RDSKSCDSS--PVSSPG--KPAPG-----DLSPSLPASPGG
BRENG1-1    CKR-E-------------RERVTRD--SGVRPTALPDSRSDGVSSSAS
```

50

ADD DATA | AUTOMATIC ALIGNMENT | MOTIF EXTRACTION —— 58 | SETTING

NO CONVERSION

FIG.12

```
                    EDIT GENE ARRANGEMENT DATA
                    10        20        30        40        50        60
              ....+....+....+....+....+....+....+....+....+....+....+....+
XLEN2MAB-1    ------------MEENEQNNREVEPQQE----SG--------EESNRG-------ILHQAPPG
BFU82487-1    ------------------------------------MANSSADENGNPPASPPPHSPVQPEDSPS
BRENG1-1      ----------------------------MEDQR-RGQGEEEDDSGSLPSPPLL-----------
BRENG2-1      ------------MDENEQSARDVEQRGAD-------ESNS--A--IRPLLQ--APG--------
BRENG2G-1     ------------MDENEQSARDVEQRGAD-------ESNS--A--IRPLLQ--APG--------
BRENG3-1      ------------MEENDHSNRDVERQDSD-------ESNR--A--ILPLLQ--APG--------
MUSEN2AB-1    MEEKDSKPSE-AAEAQROPEPSSGGGSGGG--SP--SDSDTGRRALMLPEVLQ--APG
XLEN214-1     MEENEQNNREVEPQQESQEESNRGILHQAPPGNHQPHHRITNFFIDNILRPEFQRRKEGI
                    70        80        90       100       110       120
              ....+....+....+....+....+....+....+....+....+....+....+....+
XLEN2MAB-1    NHQPHHRITNFFIDNILRPEFGRRK---------------------E------RINHQDEL
BFU82487-1    PDGP--RTTNFSIANILRPEFGARK---------------------------------
BRENG1-1      --PAHRNTDFFIDNILRPDFG--------------------------------------
BRENG2-1      NLQLPHRITNFFIDNILRPDFGRRKEANI-------------------------TRYEDN
BRENG2G-1     NLQLPHRITNFFIDNILRPDFGRRKEANI-------------------------TRYEDN
BRENG3-1      NV-LPHRITNFYIDNILRPDFGRRKEGS--------------------------RRDEIN
MUSEN2AB-1    NHQHPHRITNFFIDNILRPEFGRRKDAGTCCAGAGAGGARGGEGGAGTTEGGGGGAGGAEQL
XLEN214-1     SHQDELYTERDTGALSGAESGHHRVNVPEGAGGSSKVITVTGEKKSDLANEETLKSRGLN
                   130       140       150       160       170       180
              ....+....+....+....+....+....+....+....+....+....+....+....+
XLEN2MAB-1    FTGRDT------------GALSGAESGHHRV------NVPEGAGGSSKVITVTGEKKS
```

| ADD DATA | AUTOMATIC ALIGNMENT | MOTIF EXTRACTION | SETTING |

NO CONVERSION

GENETIC MOTIF EXTRACTING AND PROCESSING APPARATUS, GENETIC MOTIF EXTRACTING AND PROCESSING METHOD, AND RECORDING MEDIUM RECORDED WITH GENETIC MOTIF EXTRACTING AND PROCESSING PROGRAM

This application is a continuation of PCT/JP99/01693 filed on Mar. 31, 1999.

TECHNICAL FIELD

The present invention relates to a technique for automatically extracting genetic motifs, and particularly to a technique for improving a genetic motif extracting efficiency.

BACKGROUND ART

Recent progress of genetic engineering has brought rapid progress of a technique for determining a gene arrangement such as expressed by a DNA sequence and/or an amino acid sequence. Further, the genome project is being conducted worldwide so as to clarify all gene arrangements of specific organisms (i.e., to sequence or identify gene information), for various species including human being. As such, databases of gene arrangement information have increased explosively, so as to effectively utilize those previously clarified gene arrangement information (sequence gene information or genetic sequences).

Most of these gene arrangements have been clarified about the arrangement information thereof, but the functions and structures thereof are unknown. Effective methods for presuming such functions and structures of such genes from the gene arrangements include the extraction of motifs having characteristic regularities. To this end, the present applicant has proposed a technique for automatically extracting motifs by comparing a plurality of gene arrangement information with one another, in a prior Japanese Patent Application of the present applicant (see Japanese Unexamined Patent Publication No. 7-274965).

According to such a motif extracting technique, however, those extracted motifs have been merely printed out from a printer or output as a file into a database, so that the extracted motifs have not been fully reutilized in fact. As such, when adding the extracted motifs to the gene arrangement information to extract motifs again in order to promote clarification of functions and structures of genes, it has been necessary for a human operator to input the extracted motif information. However, in such a conventional technique, there has been an inevitable limitation in improvement of a motif extracting efficiency, resulting in difficulty in further improving the motif extracting efficiency.

The present invention has been carried out in view of the conventional problems as described above, and it is therefore an object of the present invention to provide a technique for improving a motif extracting efficiency for presuming functions, structures and the like of genes, by adding a mechanism for reutilizing extracted motifs.

DISCLOSURE OF THE INVENTION

As a first aspect to achieve the aforementioned object, the present invention provides a genetic motif extracting and processing apparatus comprising: gene arrangement information storing means for storing clarified gene arrangement information; gene arrangement information inputting means for inputting at least one piece of gene arrangement information; motif extracting means for extracting a genetic motif from the gene arrangement information input by the gene arrangement information inputting means; gene arrangement information retrieving means for retrieving, based on the motif extracted by said motif extracting means, gene arrangement information including said motif as a part thereof, from said gene arrangement information storing means; and gene arrangement information adding means for adding, the gene arrangement information retrieved by the gene arrangement information retrieving means, to the gene arrangement information input by the gene arrangement information inputting means.

According to such a constitution, when extracting a genetic motif, at least one piece of gene arrangement information is input through the gene arrangement information inputting means. Then, a genetic motif is extracted from the input gene arrangement information by the motif extracting means. Further, gene arrangement information including, as a part thereof, the extracted motif is retrieved from the gene arrangement information storing means, by the gene arrangement information retrieving means. The retrieved gene arrangement information is added by the gene arrangement information adding means, as required, to the gene arrangement information input by the gene arrangement information inputting means. Thereafter, motif extraction by the motif extracting means and retrieval of gene arrangement information by the gene arrangement information retrieving means are repeated, to thereby clarify functions and structures of gene arrangement information gradually. Namely, the gene arrangement information including, as a part thereof, the extracted motif can be added to the input gene arrangement information, so that the extracted motif is reutilized to thereby improve a motif extracting efficiency for presuming functions and structures of genes.

The genetic motif extracting and processing apparatus may further comprise: motif extraction range designating means for designating, in the gene arrangement information input by the gene arrangement information inputting means, a motif extraction range for the motif extracting means; wherein the motif extracting means extracts a genetic motif from within the extraction range designated by the motif extraction range designating means.

According to such a constitution, if a motif extraction range is designated by the motif extraction range designating means, a genetic motif is extracted from within the designated extraction range. Thus, from among input gene arrangement information of various organisms, only gene arrangement information of similar organisms can be designated as an extraction range, to thereby facilitate clarification of functions and structures of gene arrangements.

Further, the genetic motif extracting and processing apparatus may further comprise gene arrangement information editing means for editing the gene arrangement information.

According to such a constitution, various editions are conducted for the gene arrangement information by the gene arrangement information editing means, thereby allowing motif extraction along with an intention of a user.

In addition, the genetic motif extracting and processing apparatus may further comprise motif editing means for editing the motif extracted by the motif extracting means.

According to such a constitution, various editions are conducted for the extracted motif by the motif editing means, thereby allowing retrieval of gene arrangement information along with an intention of a user.

The genetic motif extracting and processing apparatus may further comprise alignment means for alignment-processing a plurality of gene arrangement information input by the gene arrangement information inputting means.

According to such a constitution, since the input plurality of gene arrangement information is alignment-processed by the alignment means, gene arrangement information assumed to be necessary may be input randomly, thereby enabling improvement of an input operation efficiency of gene arrangement information. Further, since users are allowed to visually understand similar regions among the input plurality of gene information, it becomes possible to readily designate a motif extraction range by the motif extraction range designating means.

The genetic motif extracting and processing apparatus may further comprise motif storing means for storing motifs; and motif registering means for registering the motif extracted by the motif extracting means into the motif storing means.

According to such a constitution, the extracted motif is registered into the motif storing means by the motif registering means, so that it becomes possible for another human operator to reutilize the extracted motif, thereby allowing improvement of a working efficiency for clarifying functions and structures of gene arrangement information.

The genetic motif extracting and processing apparatus may further comprise motif displaying means for displaying at least one motif from those motifs registered in the motif storing means.

According to such a constitution, since motifs registered in the motif registering means are displayed as required, various motifs can be readily compared with one another so that clarification of functions and structures of gene arrangements can be readily performed.

As a second aspect to achieve the aforementioned object, the present invention provides a genetic motif extracting and processing method comprising: a gene arrangement information inputting process for inputting at least one piece of gene arrangement information; a motif extracting process for extracting a genetic motif from the gene arrangement information input by the gene arrangement information inputting process; a gene arrangement information retrieving process for retrieving, based on the motif extracted by said motif extracting process, gene arrangement information including said motif as a part thereof, from a gene arrangement information database; and a gene arrangement information adding process for adding, the gene arrangement information retrieved by the gene arrangement information retrieving process, to the gene arrangement information input by the gene arrangement information inputting process.

According to such a constitution, when extracting a genetic motif, at least one piece of gene arrangement information is input through the gene arrangement information inputting process. Then, a genetic motif is extracted from the input gene arrangement information by the motif extracting process. Further, gene arrangement information including, as a part thereof, the extracted motif is retrieved from the gene arrangement information database, by the gene arrangement information retrieving process. The retrieved gene arrangement information is added by the gene arrangement information adding process, as required, to the gene arrangement information input by the gene arrangement information inputting process. Thereafter, motif extraction by the motif extracting process and retrieval of gene arrangement information by the gene arrangement information retrieving process are repeated, to thereby clarify functions and structures of gene arrangement information gradually. Namely, the gene arrangement information including, as a part thereof, the extracted motif can be added to the input gene arrangement information, so that the extracted motif is reutilized to thereby improve a motif extracting efficiency for presuming functions and structures of genes.

As a third aspect to achieve the aforementioned object, the present invention provides a recording medium recorded with a genetic motif extracting and processing program for realizing: a gene arrangement information inputting function for inputting at least one piece of gene arrangement information; a motif extracting function for extracting a genetic motif from the gene arrangement information input by the gene arrangement information inputting function; a gene arrangement information retrieving function for retrieving, based on the motif extracted by said motif extracting function, gene arrangement information including said motif as a part thereof, from a gene arrangement information database; and a gene arrangement information adding function for adding, the gene arrangement information retrieved by the gene arrangement information retrieving function, to the gene arrangement information input by the gene arrangement information inputting function.

In this respect, the term "recording medium" means a medium, which is capable of assuredly recording electronic information and also assuredly taking out the recorded electronic information as required, and which includes a mobile recording medium such as magnetic tape, magnetic disk, magnetic drum, IC card, and CD-ROM.

According to such a constitution, the recording medium is recorded with the genetic motif extracting and processing program for realizing the gene arrangement information inputting function, motif extracting function, gene arrangement information retrieving function, and gene arrangement information adding function. Thus, Those who obtained the recording medium such a program can readily construct the motif extracting and processing apparatus according to the present invention, utilizing a general computer system.

Further objects, features and advantages of the present invention will become more apparent from the following description of preferred embodiments when read in conjunction with the accompanying drawings.

BRIEF DESCRIPTION OF THE DRAWINGS

FIG. 4 is an explanatory view of the initial screen input with multiple alignment data;

FIG. 5 is an explanatory view of an edition screen;

FIG. 6 is an explanatory view of a situation where a motif extraction range is designated by arrangement;

FIG. 7 is an explanatory view of a situation where a motif extraction range is designated by a rectangular region;

FIG. 12 is an explanatory view of a situation where the arrangement to be reutilized is added to the multiple alignment data.

BEST MODE FOR CARRYING OUT THE INVENTION

The present invention will be described hereinafter in more detail, with reference to the accompanying drawings.

Figure 1:
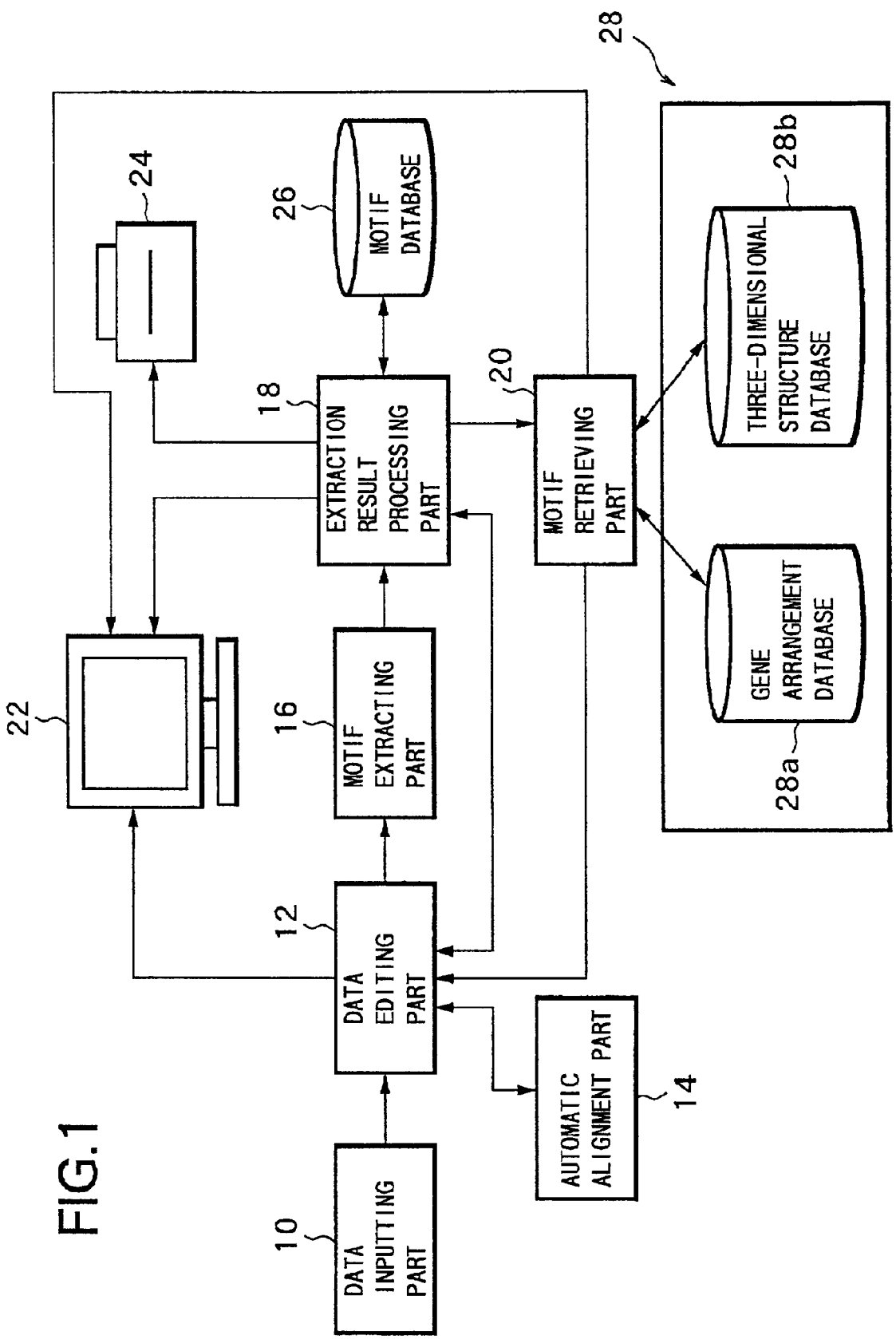
FIG. 1 is a constitutional view of a genetic motif extracting and processing apparatus according to the present invention.

FIG. 1 shows a constitution of a genetic motif extracting and processing apparatus (hereinafter called "motif extracting and processing apparatus") according to the present invention.

The motif extracting and processing apparatus is constituted of an electronic computer comprising at least a central processing unit (CPU) and a memory, and executes various processing accompanying to a motif extraction operation according to a program loaded onto the memory. The motif extracting and processing apparatus comprises a data inputting part 10 (gene arrangement information inputting means, process and function), a data editing part 12, an automatic alignment part 14, a motif extracting part 16, an extraction result processing part 18, a motif retrieving part 20, a displaying device 22, a printing device 24, a motif database 26 (motif storing means), and a gene arrangement information database 28 (gene arrangement information storing means).

The data inputting part 10 is constituted of a keyboard and a mouse, for example, to thereby provide a data inputting function for inputting at least one gene arrangement data as a motif extraction target.

For the gene arrangement data input via the data inputting part 10, the data editing part 12 provides a data editing function (gene arrangement information editing means), an extraction range designating function (motif extraction range designating means), a parameter setting function, a data displaying function, an external data inputting function, and a data reading function. To conduct various editions to the gene arrangement data, the data editing function provides an alignment achieving function based on a manual operation, such as to add a new gene arrangement data to a plurality of input gene arrangement data, to delete an arbitrary one from the plurality of input gene arrangement data, and to replace an arbitrary one of the plurality of input gene arrangement data. To designate a motif extraction range, the extraction range designating function provides functions such as to specify a gene arrangement data as a motif extraction target within a plurality of gene arrangement data, and to designate a range of aligned gene information in rectangle. The parameter setting function provides a function for setting various parameters in order to conduct an automatic motif extraction. To establish an interface between the motif extracting and processing apparatus and a user, the data displaying function provides a function for displaying the gene arrangement data under edition on the displaying device 22. To enable reutilization of retrieved gene arrangement, the external data inputting function provides a function for inputting data from the motif retrieving part 20. To effectively utilize an existing multiple alignment data, the data reading function provides a function for reading the multiple alignment data from a file.

The automatic alignment part 14 cooperates with the data editing part 12 to thereby provide a function (alignment means) for automatically aligning gene arrangement data with one another. Thus, it is unnecessary to input alignment-processed gene arrangement data into the data editing part 12, and for example, it is possible to conduct an alignment-processing by the automatic alignment function after reading a plurality of gene arrangement data from the file.

The motif extracting part 16 provides an automatic extracting function (motif extracting means, process and function) for automatically extracting a motif for a motif extraction range designated by the extraction range designating function of the data editing part 12.

For the motif automatically extracted (hereinafter called "extracted motif") by the motif extracting part 16, the extraction result processing part 18 provides a database registering function (motif registering means), a database referring function, a data displaying function and a data printing function. The database registering function provides a function for registering the extracted motif into the motif database 26. The database referring function provides a function for referring to an arbitrary motif within those motifs registered in the motif database 26. The data displaying function provides a function for displaying the extracted motif or the motif as referred to (hereinafter called "referred motif"), on the displaying device 22. Note, the database referring function and the data displaying function cooperatively constitute motif displaying means. The data printing function provides a function for outputting the extracted motif or the referred motif to the printing device 24. Further, the extraction result processing part 18 is capable of editing the extracted motif, making use of the data editing function of the data editing part 12 (motif editing means).

To retrieve gene information including therein the extracted motif from the gene arrangement information database 28, the motif retrieving part 20 provides a retrieving range designating function, a retrieval executing function (gene arrangement information retrieving means, process and function), an output-data designating function, and a data displaying function. The retrieving range designating function provides a function for designating a retrieval target motif among a plurality of extracted motifs. The retrieval executing function provides a function for retrieving the gene arrangement information database 28, based on the motif designated by the retrieving range designating function. The output-data designating function provides a function for designating a retrieval result to be added to the multiple alignment data, via the external data inputting function of the data editing part 12. Note, the external data inputting function of the data editing part 12 and the output-data designating function of the motif retrieving part 20 cooperatively constitute gene arrangement information adding means, process and function. The data displaying function provides a function for displaying data on the displaying device 22, such as to provide an interface for a user, or to display a retrieval result.

The gene arrangement information database 28 comprises a gene arrangement database 28a and a three-dimensional structure database 28b. The gene arrangement database 28a is registered with clarified gene arrangement information. The three-dimensional structure database 28b is also registered with clarified gene arrangement information which is structural information comprising a coordinate data which three-dimensionally describes the structure of the clarified gene arrangement.

Figure 2:
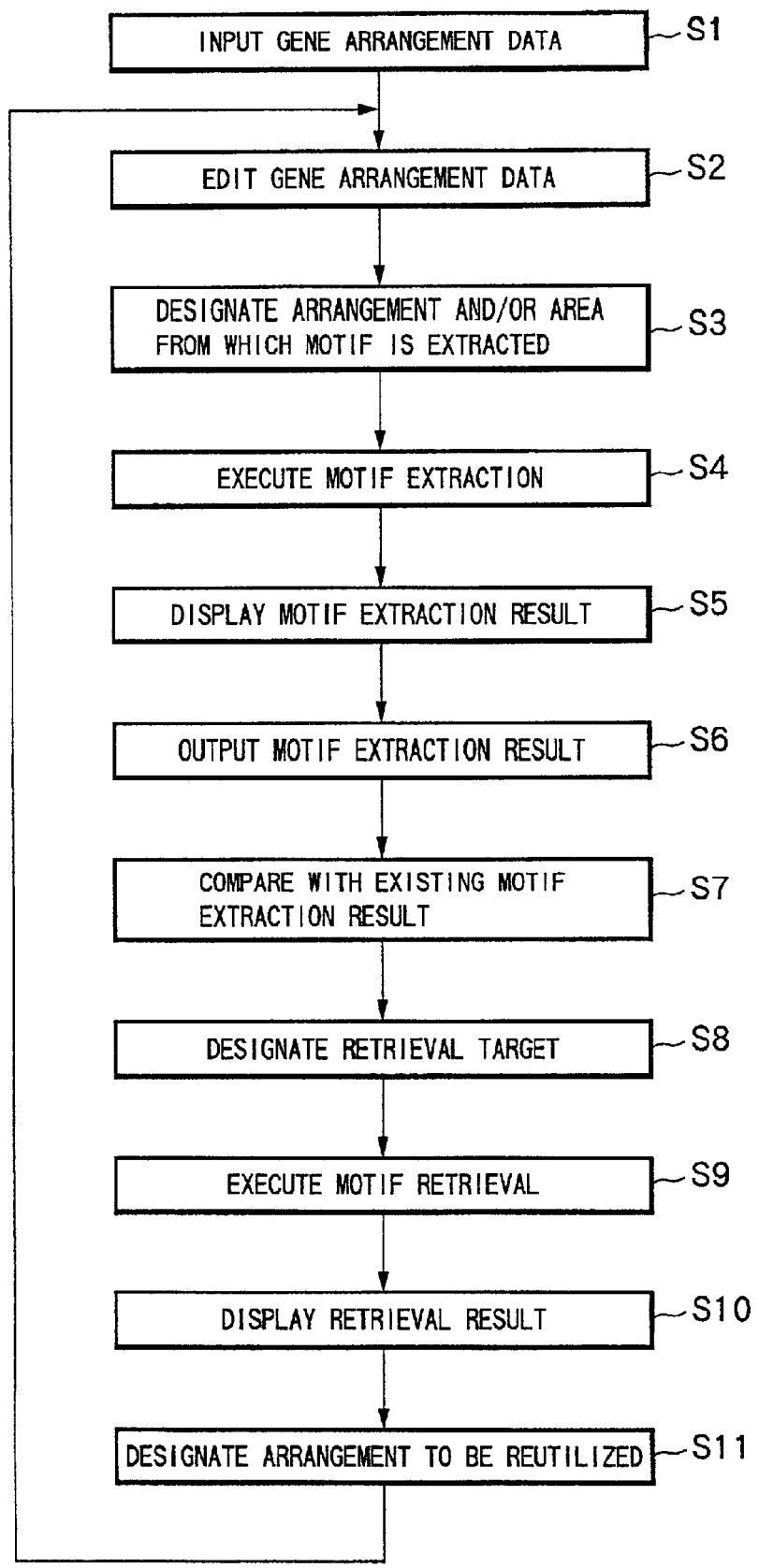
FIG. 2 is a flowchart of working procedures for conducting motif extraction.

There will be now described an operation of the motif extracting and processing apparatus having a constitution as described above, based on the flowchart of working procedures shown in FIG. 2.

At step 1 (to be abbreviated as "S1" in the figure, and so forth), gene arrangement data is input.

Figure 3:
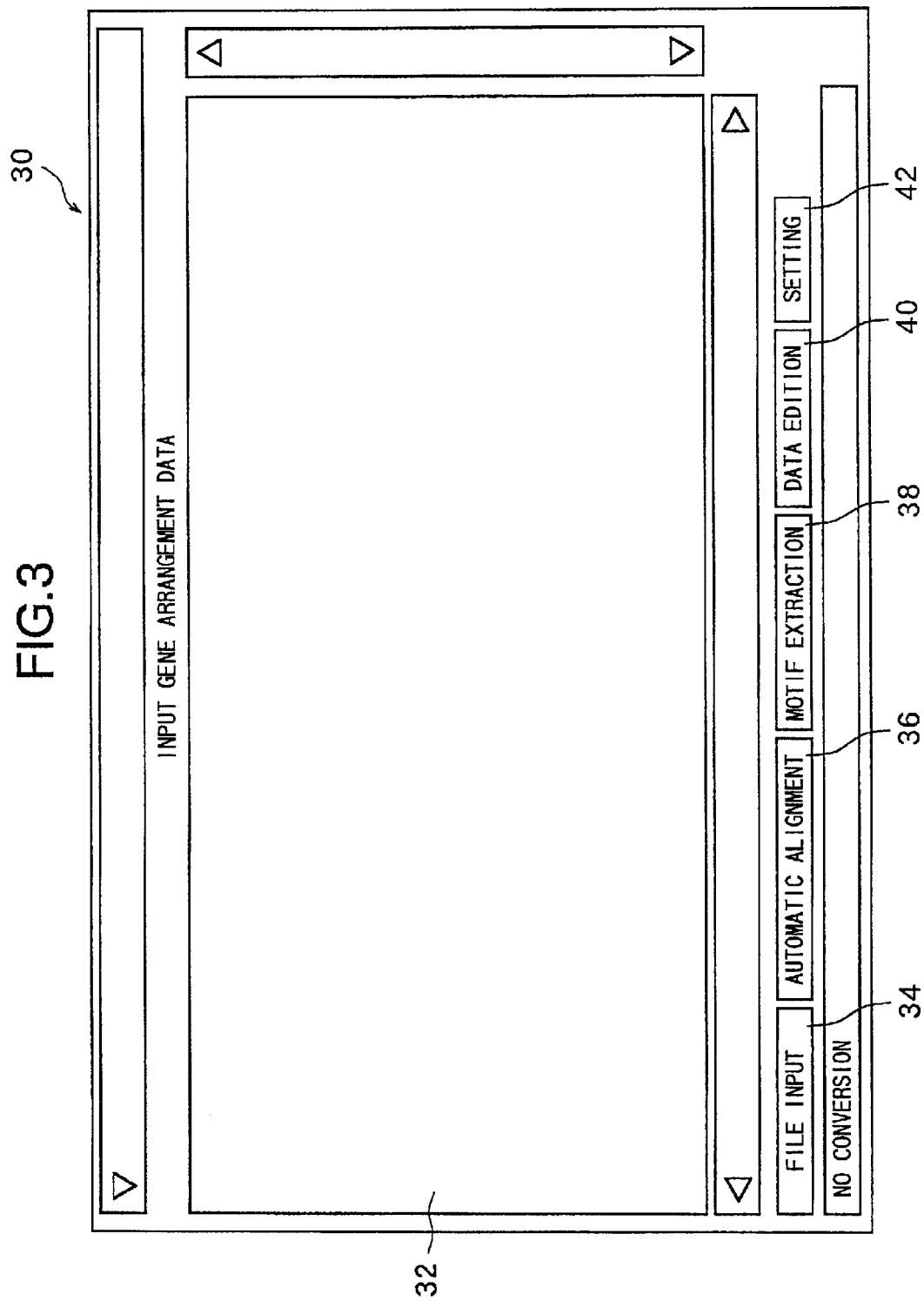
FIG. 3 is an explanatory view of an initial screen.

When the motif extracting and processing apparatus is activated, an initial screen 30 as shown in FIG. 3 is displayed. The initial screen 30 is constituted to include a data displaying part 32, a "File Input" button 34, an "Automatic Alignment" button 36, a "Motif Extraction" button 38, a "Data Edition" button 40 and a "Setting" button 42. The input gene arrangement data is displayed on the data displaying part 32. The "File Input" button 34 is clicked when the data reading function is started so as to read gene arrangement data from a file. The "Automatic Alignment" button 36 is clicked when the alignment function of the automatic alignment part 14 is started so as to conduct the alignment-processing for the input gene arrangement data. The "Motif Extraction" button 38 is clicked when the automatic extracting function of the motif extracting part 16 is started so as to automatically extract a motif from the input gene arrangement data. The "Data Edition" button 40 is clicked when the data editing function is started so as to edit the input gene arrangement data. The "Setting" button 42 is clicked when the parameter setting function is started so as to set various parameters required when extracting a motif.

To input gene arrangement data, two types of methods are provided as follows. A first method is to input gene arrangement data from a file. Namely, when the "File Input" button 34 of the initial screen 30 is clicked, a file designating screen (not shown) is displayed. Then, when a file name is designated on the file designating screen, gene arrangement data is read out from the designated file and the read out gene arrangement data is displayed on the data displaying part 32 as shown in FIG. 4. A second method is to directly input gene arrangement data, making use of the data inputting function of the data inputting part 10. Namely, when the "Data Edition" button 40 of the initial screen 30 is clicked, there is displayed an edition screen 50 for conducting various editions of gene arrangement data as shown in FIG. 5 (the details of edition screen 50 will be described later). Then, gene arrangement data is input directly through the data inputting part 10, making use of a part of the data editing function.

At step 2, there are conducted various editions of the input gene arrangement data.

When the "Data Edition" button 40 of the initial screen 30 is clicked, the data editing function of the data editing part 12 is started and the edition screen 50 shown in FIG. 5 is displayed. The edition screen 50 is constituted to include a data displaying part 52, an "Add Data" button 54, an "Automatic Alignment" button 56, a "Motif Extraction" button 58 and a "Setting" button 60. Here, the data displaying part 52, "Automatic Alignment" button 56, "Motif Extraction" button 58 and "Setting" button 60 are substantially identical with the data displaying part 32, "Automatic Alignment" button 36, "Motif Extraction" button 38 and "Setting" button 42 of the initial screen 30, respectively, and the explanation thereof shall be omitted. The "Add Data" button 54 is clicked when the data reading function is started so as to newly add gene arrangement data from a file, into the gene arrangement data displayed on the data displaying part 52.

On the edition screen 50, for example, it is possible to insert a gap (represented by "-" in the figure) into an arbitrary position, or to replace arbitrary gene information. Further, in a case that new gene arrangement data is added into the multiple alignment data, a file designating screen (not shown) is displayed when the "Add Data" button 54 is clicked. Then, when a file name is designated on the file designating screen, gene arrangement data is read out from the designated file, and the read out gene arrangement data is displayed on the data displaying part 52. Note, the gene arrangement data to be added may be the multiple alignment data.

At step 3, there is designated, if necessary, a range of the multiple alignment data from which a motif is extracted.

When no ranges are designated, the whole of the multiple alignment data displayed on the data displaying part 52 is a motif extraction target. In fact, however, there exists such a situation where only a part of the multiple alignment data is desired to be a motif extraction target. In such a situation, the range designation can be conducted by the following two types of methods so as to define a motif extraction target by the extraction range designating function. As shown in FIG. 6, a first method is to designate at least one alignment data in the multiple alignment data, by making use of a pointing device such as a mouse. As shown in FIG. 7, a second method is to designate a motif extraction target by surrounding with a rectangular region, by making use of a pointing device. Note, when the once designated motif extraction target is to be changed, another motif extraction target may be newly designated.

At step 4, automatic extraction of a motif is conducted.

When the "Motif Extraction" button 38 of the initial screen 30 or the "Motif Extraction" button 58 of the edition screen 50 is clicked, the automatic extracting function of the motif extracting part 16 is started, and a motif is automatically extracted from the multiple alignment data. If a motif extraction target has been designated at this time, a motif is extracted from within the designated range.

At step 5, the motif extraction result is displayed.

Figure 8:
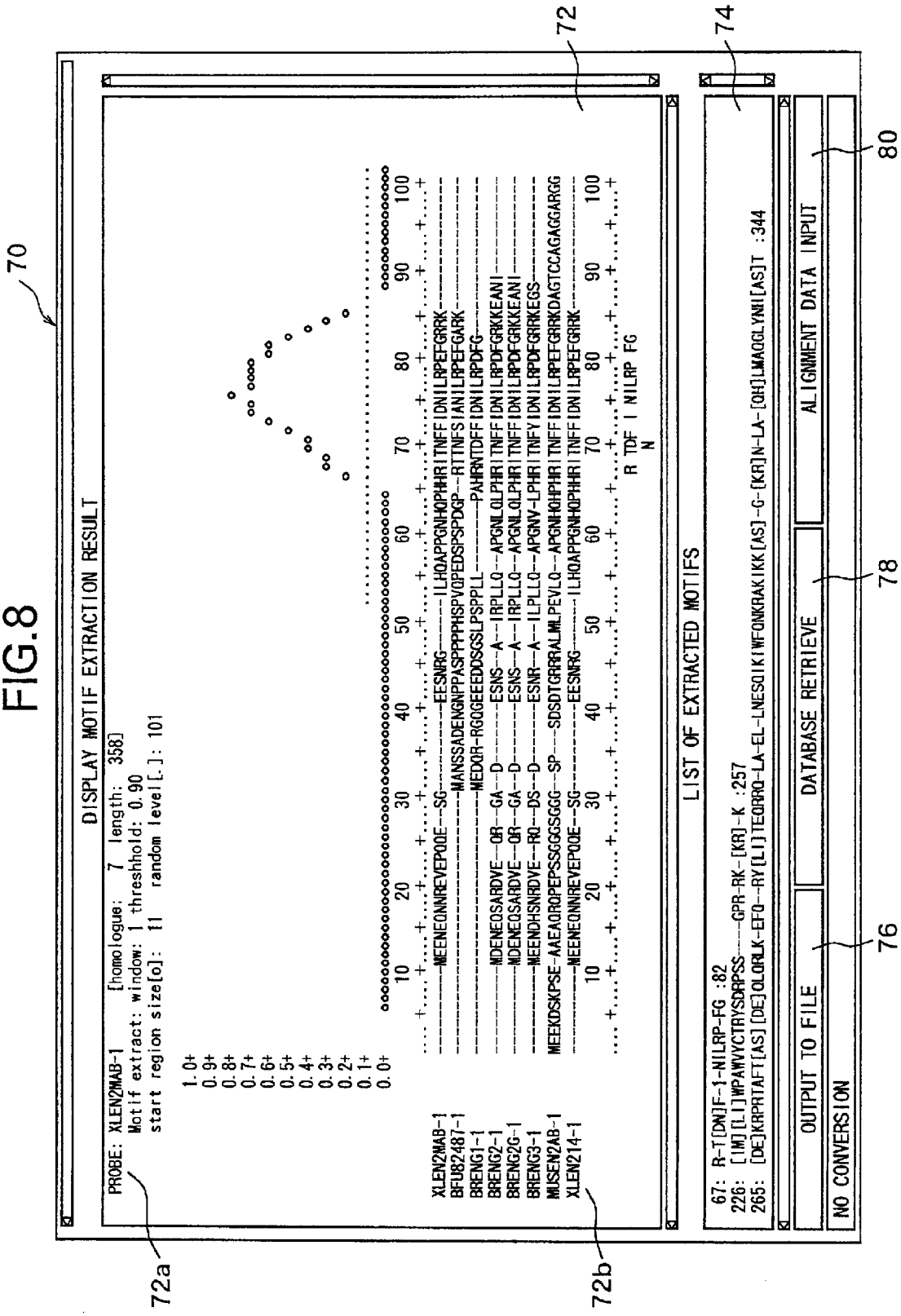
FIG. 8 is an explanatory view of an extraction result display screen.

The automatically extracted motif is displayed on an extraction result display screen 70 as shown in FIG. 8, by the data displaying function of the extraction result processing part 18. The extraction result display screen 70 is constituted to include an extraction result displaying part 72, an extracted motif displaying part 74, an "Output to File" button 76, a "Database Retrieve" button 78 and an "Alignment Data Input" button 80. An extraction parameter 72a, an analysis result 72b and the like are displayed on the extraction result displaying part 72. A list of extracted motifs is displayed on the extracted motif displaying part 74. The "Output to File" button 76 is clicked when the data printing function is started so as to output the extraction result to the printing device 24, or when the database registering function is started so as to register the extraction result into the motif database 26. The "Database Retrieve" button 78 is clicked when the retrieval executing function of the motif retrieving part 20 is started so as to retrieve the gene arrangement information database 28. The "Alignment Data Input" button 80 is clicked when the currently displayed alignment data is to be cancelled so that an alignment data is then newly read out from a file so as to conduct motif extraction.

At step 6, the motif extraction result is output.

Namely, there is conducted such a procedure outputting the motif extraction result being displayed on the extraction result display screen 70 to the printing device 24 or registering the motif extraction result being displayed on the extraction result display screen 70 into the motif database 26. In order to output the motif extraction result, the "Output to File" button 76 of the extraction result display screen 70 is clicked to thereby display an output destination designating screen (not shown) for designating an output destination. By designating an output destination on the output destination designating screen, the motif extraction result is output to the printing device 24 or registered into the motif database 26.

At step 7, there is conducted a comparison of the motif extraction result with the existing motif extraction result.

Namely, the motif extraction result is compared with the existing motif extraction result already registered in the motif database 26, to thereby conduct an operation to specify such as a gene function to be presumed by the motif.

At step 8, there is designated a retrieval target to be retrieved in the gene arrangement information database 28.

Figure 9:
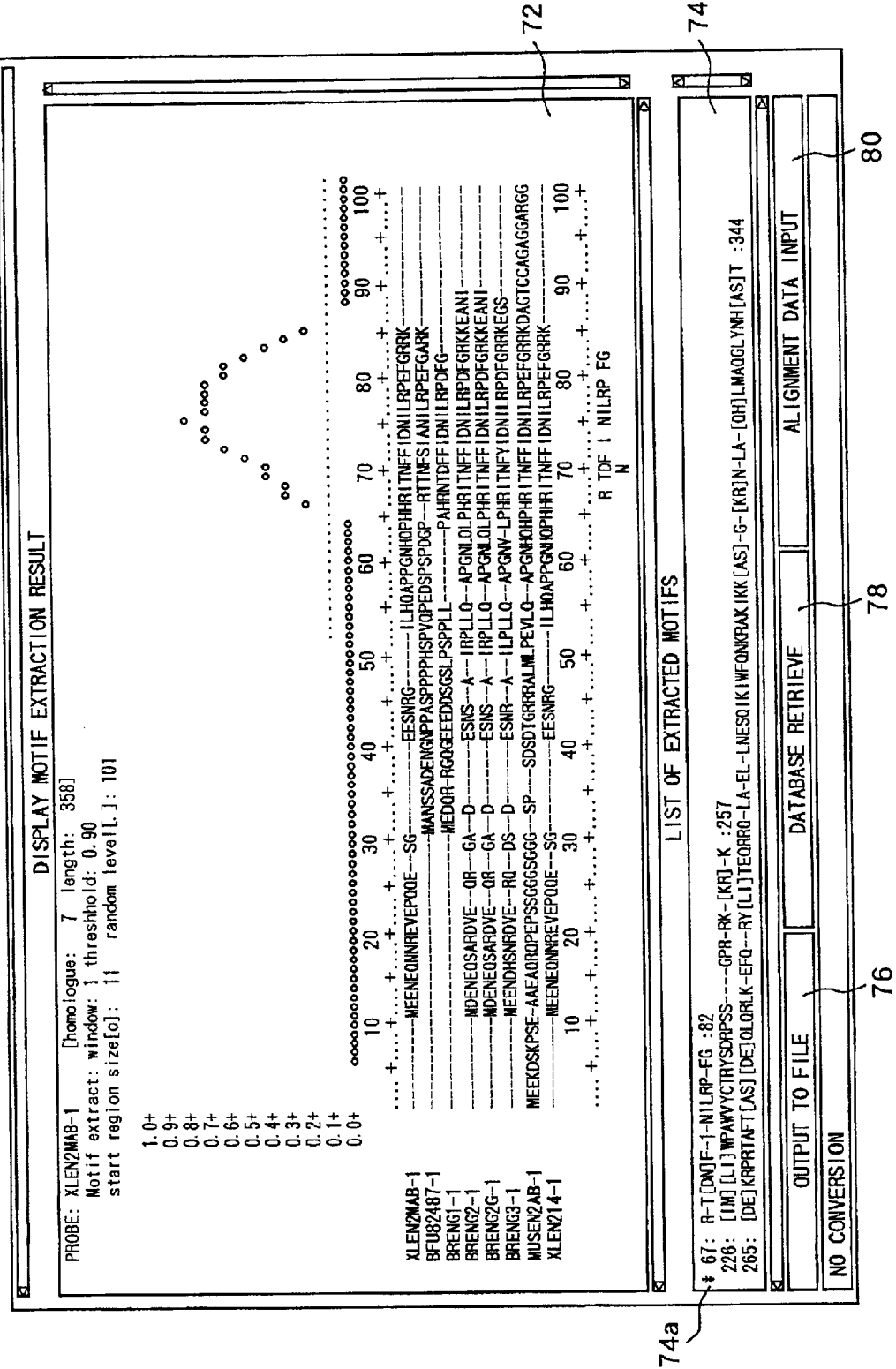
FIG. 9 is an explanatory view of an extraction result display screen where a retrieval target motif has been designated.

Namely, as shown in FIG. 9, when one of the listed motifs displayed on the extracted motif displaying part 74 is clicked, a mark 74a (depicted by "*" in the figure) is attached to a heading portion of the clicked motif so as to indicate that this motif is designated. To change the motif as the retrieval target, another motif is clicked to newly designate the same as a new retrieval target. Note, it is allowed to designate a plurality of motifs as retrieval targets.

At step 9, motif retrieval is conducted.

Namely, when the "Database Retrieve" button 78 is clicked after the motif as the retrieval target is designated, the gene arrangement information database 28 is retrieved based on the designated motif. At this time, which of the gene arrangement database 28a and the three-dimensional structure database 28b constituting the gene arrangement information database 28 is to be retrieved, can be arbitrarily selected by clicking the "Alignment Data Input" button 80.

At step 10, the retrieval result of the gene arrangement information database 28 is displayed.

Figure 10:
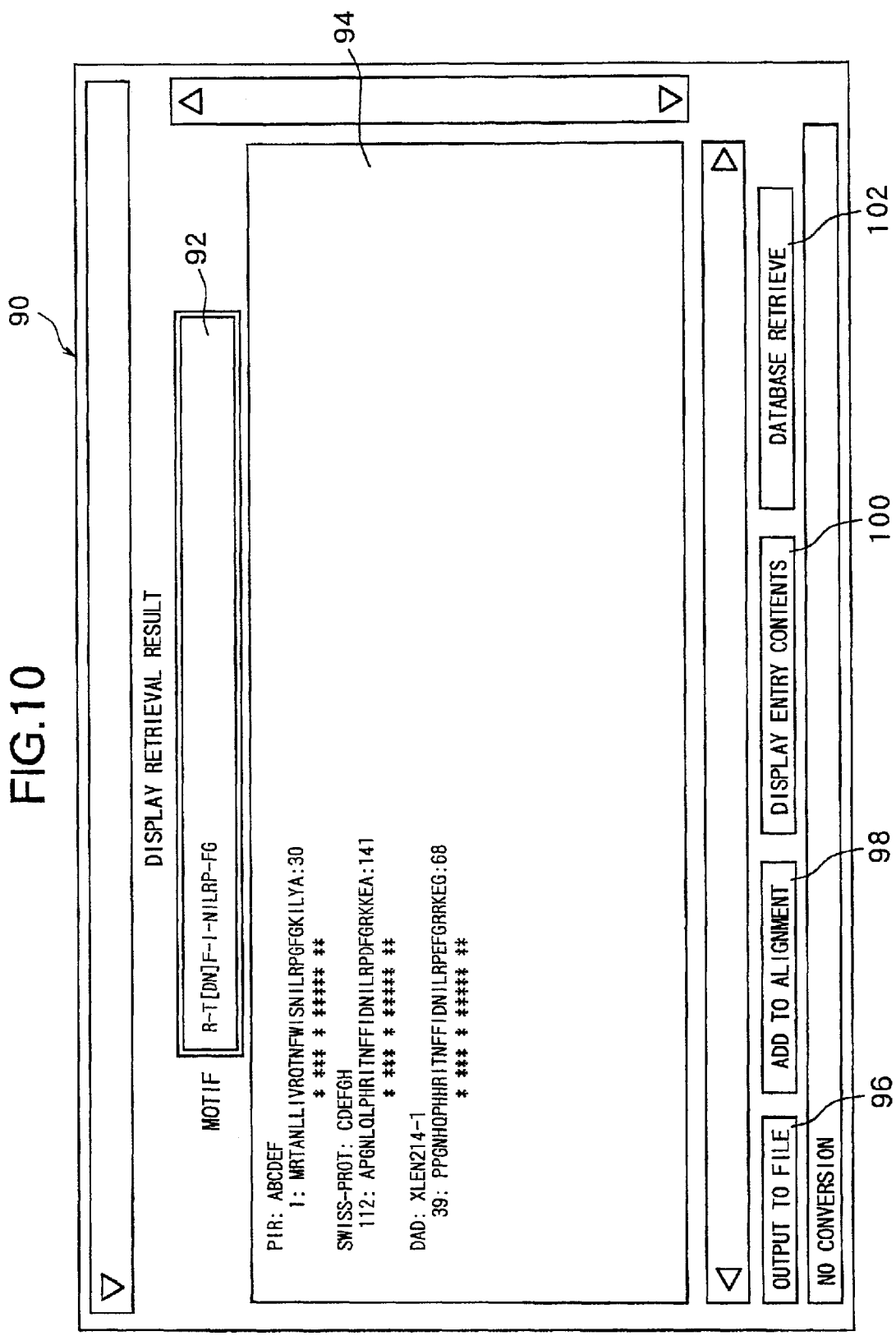
FIG. 10 is an explanatory view of a retrieval result display screen.

The retrieval result of the gene arrangement information database 28 is displayed on a retrieval result display screen 90 by the data displaying function of the motif retrieving part 20, as shown in FIG. 10. The retrieval result display screen 90 is constituted to include a motif displaying part 92, a retrieval result displaying part 94, an "Output to File" button 96, an "Add to Alignment" button 98, a "Display Entry Contents" button 100, and a "Database Retrieve" button 102. The motif as the retrieval target of the gene arrangement information database 28 is displayed on the motif displaying part 92. The retrieval result based on the gene arrangement information database 28 is displayed on the retrieval result displaying part 94. The "Output to File" button 96 is clicked when the retrieval result is to be output to the printing device 24 or registered to the motif database 26. The "Add to Alignment" button 98 is clicked when the retrieval result is to be added to the multiple alignment data, through the external data inputting function of the data editing part 12. The "Display Entry Contents" button 100 is clicked when an entry is to be displayed. The "Database Retrieve" button 102 is clicked when refining retrieval is to be conducted for the gene arrangement information database 28.

At step 11, the gene arrangement data to be reutilized is designated.

Figure 11:
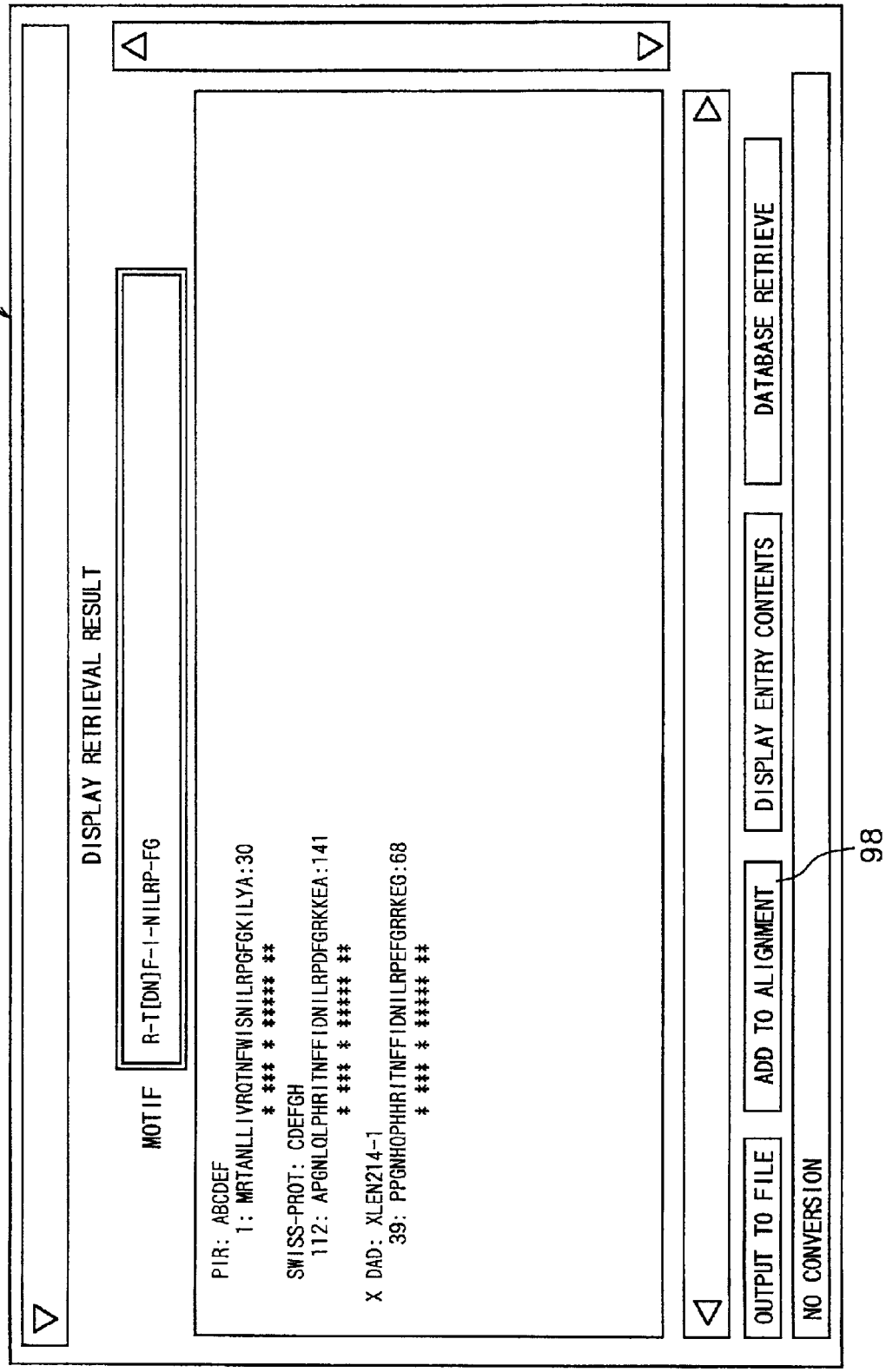
FIG. 11 is an explanatory view of a retrieval result display screen where the arrangement to be reutilized has been designated.

Namely, as shown in FIG. 11, when the gene arrangement data to be reutilized is clicked on the retrieval result display screen 90, a mark "x" is attached to a heading portion of the designated gene arrangement data. Then, when the "Add to Alignment" button 98 is clicked, the designated gene arrangement data is captured through the external data inputting function of the data editing part 12, and added to the lowermost row of the multiple alignment data as shown in FIG. 12.

Thereafter, the steps 2 through 11 are repeated to clarify functions and structures of genes.

According to the aforementioned motif extracting and processing apparatus, it becomes possible, on an integrated system, to conduct a series of processing of multiple alignment data input, motif extraction, and database retrieval based on the extracted motif. By utilizing the data editing function of the data editing part 12, it becomes possible for users to conduct precise setting for motif extraction from the input multiple alignment data. The user's interface provided by the displaying device 22 is utilized to make it possible to repeatedly perform motif extraction while visually confirming the extracted motif, and/or to perform, on the displaying device 22, comparison of the extraction result thereon with the previously executed extraction result. Further, the retrieval executing function of the motif retrieving part 20 is utilized to facilitate the database retrieval motif by motif, and the data displaying function is utilized to facilitate looking through the registered contents of the database for the retrieved data. As a result, it becomes possible to conduct motif extraction for presuming functions and structures of gene arrangements, effectively and flexibly in response to the demand of users.

By recording a program for realizing such functions into a mobile recording medium such as magnetic tape, magnetic disk, magnetic drum, IC card, CD-ROM, the motif extracting and processing program according to the present invention can be distributed in the market. Those having obtained such a medium can readily construct the motif extracting and processing apparatus, utilizing a general computer system.

INDUSTRIAL APPLICABILITY

As described above, the genetic motif extracting and processing apparatus and the genetic motif extracting and processing method according to the present invention are extremely useful, in that they can improve a motif extracting efficiency for presuming functions and structures of genes. Further, the recording medium recorded with the genetic motif extracting and processing program is extremely useful in that the same allows to readily construct the motif extracting and processing apparatus, utilizing a general computer system.

What is claimed is:

1. A genetic motif extracting and processing apparatus comprising:
   gene arrangement information storing means for storing gene arrangement information;
   gene arrangement information inputting means for inputting at least one piece of gene arrangement information;
   motif extracting range designating means for an operator to interactively designate on a display screen a motif extraction range in the input gene arrangement information;
   motif extracting means for extracting a genetic motif within the designated extraction range from the input gene arrangement information;
   gene arrangement information retrieving means for retrieving, based on the motif extracted from the input gene arrangement information, gene arrangement information including the extrated motif, from said gene arrangement information storing means; and
   gene arrangement information adding means for adding the retrieved extracted-motif-based gene arrangement information to the gene arrangement information.

2. The genetic motif extracting and processing apparatus according to claim 1, further comprising gene arrangement information editing means for editing the gene arrangement information.

3. The genetic motif extracting and processing apparatus according to claim 1, further comprising motif editing means for editing the motif extracted by the motif extracting means.

4. The genetic motif extracting and processing apparatus according to claim 1, further comprising alignment means for alignment-processing a plurity of gene arrangement information input by the gene arrangement information inputting means.

5. The genetic motif extracting and processing apparatus according to claim 1, further comprising:

motif storing means for storing motifs; and motif registering means for registering the motif extracted by the motif extracting means into said motif storing means.

6. The genetic motif extracting and processing apparatus according to claim 5, further comprising motif displaying means for displaying at least one motif from those motifs registered in the motif storing means.

7. A genetic motif extracting and processing method comprising:

inputting at least one piece of gene arrangement information for retrieval;

designating interactively on a display screen a motif extraction range in the input gene arrangement information;

extracting a genetic motif within the designated motif extraction range from the input gene arrangement information;

retrieving, based on the motif extracted from the input gene arrangement information, gene arrangement information including the extracted motif, from a gene arrangement information database; and adding the retrieval extracted-motif-based gene arrangement information to the gene arrangement information input for retrieval to repeat the retrieval process of the gene arrangement information.

8. A recording medium recorded with a genetic motif extracting and processing program realizing a process of:

inputting at least one piece of gene arrangement information for retrieval;

designating interactively on a display screen a motif extraction range from the input gene arrangement information;

extracting a genetic motif within the designated motif extraction range from the input gene arrangement information;

retrieving, based on the motif extracted from the input gene arrangement information, gene arrangement information including the extracted motif, from a gene arrangement information database; and adding the retrieval extracted-motif-based gene arrangement information to the gene arrangement information input for retrieval to repeat the retrieving process of the gene arrangement information.

* * * * *

UNITED STATES PATENT AND TRADEMARK OFFICE
CERTIFICATE OF CORRECTION

PATENT NO. : 6,745,130 B2
DATED : June 1, 2004
INVENTOR(S) : Yuichi Kawanishi et al.

It is certified that error appears in the above-identified patent and that said Letters Patent is hereby corrected as shown below:

<u>Title page,</u>
Item [73], Assignee, please change "Fujitsu Limted" to -- Fujitsu Limited --.

Signed and Sealed this

Twenty-third Day of August, 2005

JON W. DUDAS
*Director of the United States Patent and Trademark Office*